(12) United States Patent
Horvat et al.

(10) Patent No.: US 8,529,529 B1
(45) Date of Patent: Sep. 10, 2013

(54) PLACENTAL BLOOD EXTRACTOR

(76) Inventors: Branimir L. Horvat, Sarasota, FL (US);
Nevenka Horvat, Sarasota, FL (US);
Wayne G. Johnson, Sarasota, FL (US)

( * ) Notice: Subject to any disclaimer, the term of this patent is extended or adjusted under 35 U.S.C. 154(b) by 0 days.

(21) Appl. No.: 12/924,395

(22) Filed: Sep. 28, 2010

(51) Int. Cl.
*A61M 1/00* (2006.01)

(52) U.S. Cl.
USPC ........... 604/317; 604/318; 604/319; 604/320; 604/322; 604/323; 604/324; 604/325; 604/326; 604/327; 604/328; 604/329; 604/330; 604/331; 604/349; 600/573

(58) Field of Classification Search
USPC .................................. 604/317, 318, 319, 320
See application file for complete search history.

(56) References Cited

U.S. PATENT DOCUMENTS

| | | | | |
|---|---|---|---|---|
| 5,860,989 A | * | 1/1999 | Webb | 606/120 |
| 6,059,794 A | * | 5/2000 | Webb | 606/120 |
| 7,654,968 B1 | * | 2/2010 | Horvat et al. | 600/573 |

* cited by examiner

*Primary Examiner* — Tatyana Zalukaeva
*Assistant Examiner* — Ilya Treyger
(74) *Attorney, Agent, or Firm* — Frank A. Lukasik

(57) ABSTRACT

A placental blood extractor consists of an outside box having plurality of plastic bags for compressing the placenta and mounted to the top of the box. The lower part of the box has possibility to use several different circularly movable plates for mechanically facilitating the flow of the blood in the collecting veins on the fetal side of the placentas toward the central main umbilical cord vein. The box has an opening in the central lower part of the box and the lower area mechanical tray for the umbilical cord to exit the box. Blood is collected from umbilical cord and is to be collected into commercial collection bags. The area of the bag for collection of blood may be under negative pressure to facilitate the collection of blood but also gravity force may be used for that purpose. Both, the first part with the compression chambers as well as the second part, the Collector of Blood have pumps and manometers controlled by computer in their operations.

1 Claim, 12 Drawing Sheets

PLACENTAL BLOOD EXTRACTOR

FIELD OF INVENTION

This invention relates broadly to medical instruments, and more particularly, this invention relates to an umbilical cord blood extractor that extracts blood from umbilical cords and placenta. The blood is extracted after the placenta is delivered after the birth of the child. This blood contains many important components for use in medicine.

STATE OF THE ART

The umbilical cord serves as the conduit between a mother and a fetus developing in the womb of the mother. Circulation in the fetus/baby, umbilical cord and placenta is totally separate from the mother's blood circulation. If any mixing occurs, this results in severe illness for the baby as well as the mother. Nutrients and oxygen within the blood of the mother are absorbed in placenta and delivered through the blood in the umbilical cord to the fetus; metabolic waste products and carbon dioxide from the fetus are absorbed in the placenta and extracted by mother. Immediately after a baby is born, the umbilical cord is clamped to stop the flow of blood through the umbilical cord, it is cut to free the baby, and after that the placenta is expelled from the mother's uterus.

Umbilical cord blood has been collected for many different reasons, one of which is that it contains significant number of stem cells. They are used in many therapeutic and experimental procedures. Obtaining the placental blood is a cumbersome problem as well as results in a rather small amount of the collected blood. This process is presently done in most instances by "milking" the umbilical cord.

A quick method of obtaining the blood from the cord is to manually "milk" blood from the umbilical cord; i.e., to squeeze the section of the umbilical cord by hand close to placenta to rapidly and thoroughly remove blood from the cord. However, this is not usually practical. The umbilical cord is coated with various fluids, e.g., vaginal blood which contains bacteria, amniotic fluid, and Wharton's gel, making the cord slippery and hard to handle it efficiently. Furthermore, it is desirable to minimize contact between health care workers and such fluids. In fact, U.S. federal laws and regulations of various other agencies have mandated protecting health care workers from contact with blood and its possible pathogens.

The usual amount of blood obtained through this process, as well as by using devices mentioned further, is from 40 cc to 70 cc, very rarely over 100 cc, when it is successful. However, these amounts of blood collected are mostly corresponding to the blood contained in the umbilical cord. Longer the cord, more blood is retrieved. Up to now the extraction of blood from the placenta is mostly unsuccessful as will be discussed later. For that reason a number of devices have been patented for taking blood from the umbilical cord that does not require manual "milking" the cord. However, none of them are in any wide use or are produced for that purpose (see further discussion).

U.S. Pat. No. 5,356,373 by Dracker describes aspiration of umbilical cord blood for use in later autologous transfusion for the baby. Almost all of the aspirated cord blood comes from the umbilical cord vein and, may be small amount from the collecting veins of the placenta. Due to the way the blood is aspirated, we have some questions whether this is even patentable because it does not give any information aside from application of vacuum aspiration, actually application of negative pressure (which is not patentable in our opinion because this way of obtaining blood has been practiced by physicians for literally centuries) which is being done in conventional blood banks.

U.S. Pat. No. 5,575,795 to Anderson discloses an umbilical cord holder having an elongated portion with the curved open trough and clamps at either end of the elongated portion. A health care worker places the umbilical cord onto the trough and seals the ends of the umbilical cord with the clamps. While holding the elongate portion, the practitioner inserts a needle through the open trough and into the cord vein and, using a syringe, withdraw blood from the cord. This device extracts the blood exclusively from the umbilical cord, more specifically from the umbilical cord vein as the first quoted patent essentially does.

U.S. Pat. No. 5,860,989 by Webb discloses umbilical cord blood extractor which includes a lower tray for receiving the cord and an upper lid for squeezing the cord, each having a hinged end and a free end. The lower tray and the upper lid are connected by a live hinge at their hinged ends. The lower tray is further provided with a longitudinal trough and a distal blood reservoir for collecting blood. A blood collection needle is preferably provided in the lower tray at a lower portion of the reservoir. The upper lid is formed with a longitudinal protrusion sized in such way that when the upper lid is rotated about the hinge, up and toward the lower tray, the plunger enters into the trough. Again, the collected blood is coming exclusively from the cord and no blood is really collected from the placenta.

U.S. Pat. No. 5,919,176 by Kuypers et al., describes an apparatus where there is a single pressure bag applying the pressure on placenta. Due to that pressure, any ability to extract blood from placenta and collecting veins is impossible because this pressure essentially closes the collecting veins and all blood which is then collected comes from the umbilical cord vein. Also, there is a question if the "holder" for the umbilical cord is of any real help. The umbilical cord is a flimsy organ with tortuous vessels and any pressure will cause stoppage of the blood flow. We are not aware that anybody really uses it or produces this apparatus for the same reasons which apply to the previously mentioned devices (probably due to the problems which we addressed).

U.S. Pat. No. 6,059,794 by Webb discloses an umbilical cord blood extractor which includes a lower tray for receiving the cord and an upper lid for squeezing the cord. The lower tray is provided with a longitudinal trough and a distal blood reservoir for collecting blood. The trough is closed at its proximal end and opens into the reservoir at its distal end. A blood collection needle is preferably provided in the lower tray at a lower portion of the reservoir. The upper lid has a longitudinal protrusion (plunger) sized such that when the upper lid is rotated toward the lower tray, on the pivots or at the hinge, the plunger enters into the trough and squeezes a section of the umbilical cord located therein. This device also collect the blood exclusively from the cord and no blood is really collected from the placenta.

U.S. Pat. No. 6,302,854 by Paderni describes again an apparatus where there is a single pressure bag applying the pressure on placenta. Due to that pressure, any ability to extract blood from placenta and collecting veins is impossible because this pressure essentially closes the collecting veins and all blood which is then collected comes from the umbilical cord vein. Also, there is a question if the "holder" for the umbilical cord is of any real help. The umbilical cord is a flimsy organ with tortuous vessels and any pressure will cause stoppage of the blood flow. Again, we are not aware that anybody really uses it or produce this apparatus (probably due to the problems which we addressed).

U.S. Pat. No. 7,654,968 by Horvat et al. describes an apparatus where there is a plastic box containing several circular pressure chambers applying the pressure on placenta placed between two sets of the chambers. The pressures in the chambers are decreasing in the level from the most peripheral one to the central one. Due to that decreasing pressures, the blood in the collecting veins flows from the periphery toward the central umbilical cord vein and is then extracted to the commercially available sterile bag.

SUMMARY OF THE INVENTION

A. It is therefore an object of the invention to provide an apparatus for rapidly extracting blood from placenta and umbilical cord.
B. It is another object of the invention to provide an apparatus that minimizes contact between a practitioner and umbilical cord and placental blood being extracted from the umbilical cord.
C. It is further an object of the invention to provide an apparatus, which is relatively inexpensive and easy to manufacture, and which efficiently extracts blood from an umbilical cord and placenta.
D. It is further an object of the invention to provide an apparatus, which is functions with relatively limited involvement by its operators.
E. A still further object of the invention is to dramatically increase the amount of the extracted blood by
  1. using sequentially lower pressurization of placenta on the maternal side of the placenta and delivering the blood from placenta to the collecting veins on the fetal side of the placenta and then
  2. using mechanical means to "push" the blood in the collecting veins on the fetal side of placenta toward the umbilidal cord vein from where it would be collected and then new blood would be pushed again into collecting veins on the fetal side of placenta.

These objectives will be discussed in details below, a Placental Blood Extractor (PBE) is provided and broadly comprises means for receiving the placenta, means for receiving the cord, means for extracting the blood from the placenta and umbilical cord and collecting the blood into conventional commercial collection receptacles.

The proposed Placental Blood Extractor (PBE) for collection of umbilical and placental blood is designed to be very simple and mostly automatic and controlled by computer in its operation. We expect that the amount of the collected blood will allow us to use other components of the blood for therapeutic use like red cells, platelets and other residual components. The invention comprises of (these components will be described in details in later text):
  an outside firm plastic box for placing placentas and umbilical cords,
  soft plastic bags lining this upper portion of the box for compression of placentas (compression bags) to facilitate that blood is "pushed" from the placental vessels into the collecting veins,
  pumps for exerting air pressure in the compression bags,
  valves between the pumps and bags,
  manometers for measuring the achieved pressures,
  in some of our options sterile bags where the placentas are placed prior to pumping procedures with a tube for insertion of umbilical cord (the option when non-sterile lower trays are used);
  lower disc(s) on which the placentas will be placed and is used for facilitating the mechanical "push" of the blood from the collecting veins on the fetal side of the placentas to the umbilical cord vein.

One of the options we offer for protecting placenta from compression bags and the rotating
  lower tray is that we cover the maternal side of placenta with a sterile plastic sheet which may have firm protrusions to keep the placenta in place while the lower tray is rotating and the fetal side of the placenta is placed on another sterile plastic sheet and then on a sterile disc with ridges for extraction of the blood from the collecting veins on the fetal side of the placenta toward the umbilical cord vein.
  A regulatory computer for controlling the level of the pressure in the compression bags as the blood is being extracted from the placenta.
  In the box for Collection of Blood (COB) is
  conventional commercial plastic bag for the collection of human blood,
  a negative pressure maintained by a separate pump which is used to facilitate the extraction of blood from the umbilical cord, also operated by the computer.

Instead of COB, gravity may be used for collecting the blood from the umbilical cord and before ending the collection, manual "milking" of the residual blood may be done.

Some of the parts of the device are in present uses in medical devices and we do not claim priority for these parts but they are used for describing the entire system of collection of blood using our new as well as known components which make this device functional.

One has to understand the placenta and umbilical cord is a closed circulatory system because any mixing of maternal blood with the fetal blood would cause severe problem for the baby as well as the mother. If the mother or child are not infected prior to the baby's delivery, the placenta provides biologically sterile blood basin comparable with the condition when the blood is drawn from the adult blood donors. Thus, no maternal blood can be mixed with the fetal blood if there are no tears in the placenta.

DETAILED DESCRIPTION OF THE COMPONENTS OF THE INVENTION

The instant invention, a Placental Blood Extractor (PBE), for collection of the umbilical and placental blood has a simple operation. It is composed of the Placental Blood Extractor (PBE) and the Collector of Blood (COB). The entire system is composed of some easily maintained parts.
A. The system consists of:
The outside firm plastic box is round in shape (FIG. 1, FIG. 10, FIG. 11, FIG. 12), and depending if only one type of this box should serve all processed placentas, then being larger, or if more PBEs are produced for different sizes of the placentas, then different sizes may be selected. Thus, this box may be from six to twelve inches in outside diameter. The box has two parts, the upper and lower parts which are to be closed when placenta is placed in this box and the operation is to start. The lower part has an opening where the umbilical cord is lead outside of the box.
1. Plastic soft compression bags lining the upper portion of the above described outside box (FIG. 2, FIG. 3). This part is constructed of several separate bags, all being concentric. Each separate bag has its own inflation channel. Upper parts of the compression chambers are attached to the wall of the upper portion of the firm plastic container and lateral sides are in contact with other neighboring bags. The bottoms of the bags function to pressurize the placentas. When there is no placenta in PBE, the inflated plastics bags should meet the lower tray area. When compression chambers are not inflated, placentas can be placed into PBE and the box can be closed (FIG. 10).

2. Lower plate of PBE. There are several possible options of this lower part of PBE and we have selected several different modifications helpful to facilitate the collection of blood from the placenta. However, other modifications in the range of the ones presented are possible to be done as well. The main point of the lower plates is to mechanically extract blood from the collecting veins on the fetal side of placentas toward the umbilical cord vein from where it is aspirated into commercially provided collection bags with appropriate anticoagulant.

a. The first choice (FIG. 4) is constructed of two plastic discs with the outside diameter of the inner diameter of the firm plastic box and the inner diameter of the middle part of the area where the umbilical cord is to be lead from the firm plastic box for placing placenta. The lower disc is firmly attached to the lower part of the rigid plastic box containing the compression chambers. The upper part of this choice of discs is driven by a motor which causes the rotation of this upper disc. The upper disc has several rollers which have axles attached to the upper disc and are protruding above the surface of the upper disc as well as below this upper disc in contact with the lower part of the disc resulting in rotation of the rollers. The upper disc is driven by a motor which causes the rotation of this disc. Due to the contact of the rollers with the lower disc, the rollers are turning in the direction of the movement of this disc. These circular movements of the rollers against the fetal side of the placenta and the collecting veins on its surface push the blood in the collecting veins centrally. This causes that blood is finally drawn into the umbilical cord vein from where it is then extracted.

b. The second choice is composed of three discs (FIG. 5.). The first one, the lowest one, is firmly attached to the firm plastic container where the placentas will be placed. The second one is composed of two connected parts of the discs. One part being circular in shape and positioned between the first disc attached to the rigid plastic container and upper part of this second disc residing above the third disc. Thus, one part of this "dual" disc is below and another one is above the third disc. The third disc will move circularly by a motor attached at the outside of the box. This upper third movable disc has attached several tubular protrusions above its surface in the heights from 0.5 to 1.2 cm. The peripheral parts of the protrusions are attached to the outside of the third disc with a possibility to be slightly angled when the central parts of the protrusions are moved. The central part of these protrusions are residing in the somewhat wider indentations of the upper part of the second disc. The movements of the third disc cause friction between the first disc and the lower part of the second disc. This results in a delay in the movement of the second disc. This also results in the delay of the movement of these central parts of the tubular protrusions. Due to this, the protrusions are tilted peripherally ahead of the central parts of these protrusions. Because of this, the protrusions are positioned in such a way to push the blood in the collecting veins on the fetal side of the placenta centrally toward the umbilical cord vein. When the direction of rotation of the third disc is reversed, similar but opposite result is achieved. Again, in this reverse movement the blood is again being "pushed" toward the umbilical cord vein. The third disc has enough open spaces to allow the protrusions to move their central parts from one direction to another. These spaces are covered with the extensions protruding from the tubular protrusions residing on the third disc and protecting the placenta from falling into these open spaces.

c. Third possible choice is to be constructed as a single disc (FIG. 6 without circular lines) with protrusions ("ridges") above its surface in the heights from 0.5 to 1.2 cm (in this description disregard the circular lines in this drawing—see next "d" section for explanation). Between these protrusions are depressions separating these protrusions from each other. The peripheral parts of the ridges are tilted toward the movement of the disc. The protrusions of this lower disc are of different length (#19) to allow enough space for depressions between all protrusions to enable the blood to be drained from the placenta into the collecting veins and then to be pushed mechanically toward the umbilical cord vein. Due to this positioning of the protrusions they will "push" the blood in the collecting veins on the fetal side of the placenta centrally toward the umbilical cord vein and allow them to be again filled with blood from the placenta. The disc will be rotated by a motor attached at the outside of the container and, as stated before, the "ridges" above the surface of the disc will "push" the blood centrally toward the umbilical cord vein.

d. Another modification for the lower plate described under "c" (FIG. 6 with lines of separation between the rings) is that the disc is composed of several individual rings commensurate to the number of the compression chamber above each individual ring. The rings are initially in a lower position and, when the compression bag above the ring is inflated, this particular ring is elevated for 0.5 cm to 1 cm from the previous position to be in the same level as is previous ring already in operation. Only the elevated rings will move circularly and the rest of the rings (one or more than one) where there is no pressurized compression bag above it will be stationary (FIG. 7 shows the construction of the lower area where mechanism for rising or lowering the rings is located). When the time of the first ring of circulation is completed, the compression chamber pressure above the second ring is being pressurized and the corresponding ring of the lower plate is elevated in the level of the first ring. The pressure of the second compression chamber is to be lower than is the level of pressure in the first compression chamber, which remains inflated and its ring keeps rotating. Now the first and second rings circulate together. The same is to happen with the next circular ring when time comes to be elevated and the compression chamber above is inflated (again with lower pressure than previous compression chamber), etc. This is repeated until all rings are engaged in the movements and pressurization of all compression chambers is finished for this cycle. When the time of the first cycle of pressurization of all compression chambers is finished, all compression chambers except the first one are deflated and all corresponding rings are placed in the initial depressed position. Then the next cycle is initiated and the procedure is repeated. This will assist that the blood in the collecting veins is "pushed" toward the central vein of the umbilical cord for extraction from them.

e. The fifth choice is composed of several concentric discs each to be moved in the opposite direction from the previous and the next concentric ring (FIG. 8). Each of the rings contains the "ridges" followed by indentations.

However, the direction of the protrusions are always in such a way that the peripheral part of the ridges are tilted toward the circular movement of this concentric ring and the central part is tilted behind the peripheral part of the ridge. The ridges above the surfaces of the concentric rings measure in the heights from 0.5 to 1.2 cm. They are separated from each other by several centimeters of distance from the height of one to the height of the next protrusion. A motor placed outside of the container for the placenta will have two axels. One axel of the motor will move circularly first, third and fifth circular ring (in case when there are six circular rings) in one direction and the other axel, connected with the first one but running in the opposite direction, will keep turning the second, fourth and sixth ring in the opposite direction. All these rings will keep pushing the blood in the collecting veins of the placenta toward the central umbilical cord vein. Movements of the rings may be done by separate motors for each individual or group of the rings as well.

f. Another choice of the lower plate is constructed of two discs (FIG. 9). One plate is placed at the bottom of the lower part of the round firm box for placing the placenta and is in direct connection to the motor which move this plate. Above this plate is another plate (which may be designed to be used as sterile plate and will be placed to be used before any new extraction is attempted) and this plate will be moved by the lower one. This upper plate will have protrusions which will measure from 0.5 cm in height to 1.2 cm in height. However, these measurements may be altered as per experience of the operators. Between each of the protrusions will be a depressed area. When the protrusions move the blood from the collecting veins toward the umbilical cord vein, the pressure of the compression chambers will extract additional blood from the placenta into the collecting veins in these depressed areas of the plate and the next protrusion will again extract the blood toward the main umbilical cord vein. The upper part of the plate may be taken out from the machine and sterilized for the next extraction of the blood if designed as such.

4. Valve(s) between the pumps and compression chambers.

There are several valves controlling the inflation of individual compression bags. Also, there are two way valves to control either pumping or deflating the bags. This valve(s) in some cases may be capable to inflate all compression chambers concurrently or allow them to be all deflated as well as to inflate or deflate compression chamber. The software of the controlling computer operates all valves.

5. Manometers for measuring the level of pressure for each of the compression chambers.

These manometers are connected by channels pumping the compression chambers prior to the valves and provide the information to the computer about the achieved pressures in the bags. Computer monitors the pressure only when valves for particular compression chamber are open. Manometers measure continuously the achieved pressure in each of the compression chambers, record them and release this information to the computer. Due to this information, the computer software is able to maintain the appropriate level of pressures. If the pressures in the compression chambers change at any time during the operation of the PBE, computer corrects it through commands by its software to the pump(s) and valves.

6. Sterile bags for placement of the placentas will be always used when plates for mechanical extraction are not sterile. They are to be placed between the upper part of PBE and the lower area of PBE. The sterile bag has a protrusion for the umbilical cord which is placed through the central part of the lower area of PBE. These are commercially manufactured plastic sterile bags for placement of the placentas prior to placing them in PBE. These bags will minimize the handling of the placentas by the operator and minimize the possibility of contamination. The edges of these plastic bags have extensions which are placed between the upper part and lower part of the firm plastic box for placing the placenta and this way secure the placenta that it does not change the position during the extraction of blood.

7. In case that a sterile lower plate for positioning the placenta is used, a sterile sheet of plastic is used to cover the maternal side of the placenta and separate it from the compression chambers. This plastic sheet has protrusions toward the placenta which hold the placenta in place while the plate is rotating. Another sterile plastic sheet is placed between the fetal side of the placenta and the lower rotating tray. The edges of both of these sheets are secured when the form plastic box is closed.

8. Regulatory computer maintaining the operation of PBE as well as operations of COB which is later described.

B. The other part of Placental Blood Extractor is Collector of Blood (COB) and it is composed of (FIG. 11):

1. Transparent firm plastic box for commercially available blood collection bags with anticoagulant.

Transparent firm plastic box for insertion of the sterile commercial collection blood bags for the blood serves the purpose of being able to decrease the pressure in this box and facilitates the collection of the blood from the umbilical cord vein into the sterile bag. This low negative pressure facilitates the flow of blood from the umbilical cord vein to the sterile collection bag where the anticoagulants are present to prevent any coagulation of the collected blood.

Transparent box serves the purpose that the operator has a continuous visual control of the operation of the equipment.

2. Negative pressure Pump.

This negative pressure pump produces the negative pressure in the Collector box.

Negative pressure serves that the commercially supplied plastic blood collection bag the most efficiently aspirates the blood from the umbilical cord vein. This results in continuous flow of all blood from the umbilical cord without damaging the collected cells. The pump is operated through the computer software designed for that purpose.

3. Manometer for measuring the negative pressure in COB.

Manometer measures continuously the achieved pressure, records it, and releases this information to the computer. Due to this information, the computer software is able to maintain the appropriate levels of pressure in COB. If it is changed any time during the operation of PBE the computer software then directs the pump to decrease or increase the pressure as needed during the collection of blood.

4. Commercially available mechanism for gentle shaking of the box (agitator) for mixing of the blood with the anticoagulants.

The COB box is placed on the mechanism for gentle shaking of the COB box with the sterile collection bag. This mechanism gently shakes the transparent firm plastic box and the inserted bag for the collection of blood facilitating the mixing of the anticoagulant with the collected blood. This shaking is present during the entire operation of the collection of the placental and cord blood. Also, an agitator may be placed inside of COB if COB is differently constructed.

5. COB, agitator and collecting bags may be placed on a weighing equipment which will accurately record the amount of collected blood and deliver this information to the computer to be used for final report to be made after the end of each collection of blood.

COB may not be used if gravity is used for collection of blood into commercially supplied blood bags. In such case the operator will "milk" the umbilical cord at the end of the drawing to collect any residual from the umbilical cord.

6. Computer software for the operation of COB (the same computer regulates and operates PBE).

Computer software controls the negative pressure under which the collection of the blood from the placenta and the umbilical cord is done. Computer software directs the function of PBE and COB to collect the blood from the placenta and the umbilical cord in as short time as possible and as uniformly as possible for the operators. It manages the levels of the pressure applied to different chambers of PBE, duration of time of these pressures, and controls the level of pressure in COB. At the end of the operation the computer will issue a report to the operator with all information regarding the collection.

7. Printer for issuing detailed report to the operator with wireless telephone connection to the central data collection area and blood bank where the blood is to be processed.

8. Commercially available sterile tubing with the sterile needles (plastic or stainless steel) and sterile commercially available bags connecting the vessels of the umbilical cord and the commercially available sterile collection bags for the blood collection. These are the commercially available items.

General Principles and Restrictions in Operation of the Equipment

Operators of PBE (and COB) are able to make certain modifications of the operations of PBE and COB. They are allowed to modify the following parts of operation:
1. Total time of the collection (aside from the restriction in the further list of these restrictions).
2. Time of the individual pressurization of the compression chambers and time of movements of the discs or rings.
3. Modify pressures in the different bags for pressurization of the placenta.
4. Modify the negative pressure level in the transparent firm box of COB.
5. Levels of gentle shaking of the COB.

The operators of PBE (and COB) are restricted in making certain modifications of the operations of PBE and COB. As per computer software, they are not allowed to modify the following parts of operation:
1. Time of the collection should not exceed 25 minutes due to the possible coagulation of the blood in the placenta and the umbilical cord. However, future modifications may be dictated by the results of actual obtaining of blood.
2. Reverse the pressure in the bags for pressurization to result in the lower pressures in the peripheral bags and higher in the central ones. This will result in accumulation of blood in the periphery of the placenta and obstruction of the flow of blood toward the umbilical cord.
3. Increase the shaking of COB above the levels suggested by the manufacturer. This may mechanically damage the cells collected in the bag.

Steps in Operation of the Equipment

1. Operator visually inspects PBE that all inflation bags are deflated. If this is not the case, the operators deflate the bags through order into the computer or even may do it manually. This part of operation is not recorded as the start of the operation.
2. Prior to handling placenta, operator places the sterile blood collection bag into COB and attaches the exposed commercially available kit for connection of the collection bag and the vessels of the umbilical cord. The cover of the plastic or stainless needle for insertion into the umbilical cord is not removed at this point. Operator visually inspects the bag for the presence of the anticoagulant in the bag.
3. a. Placenta is placed into the sterile bag and the umbilical cord is threaded through the central extension for it. The placenta with the bag is placed into the round firm box and the umbilical cord is led through the centrally placed opening in the box for it. The terminal end of the plastic extension for umbilical cord is cut, umbilical cord is pulled out of the round firm plastic box and placed on a sterile surface. The umbilical cord is cleansed as the surgical procedure demands. The needle for evacuation of blood from the umbilical cord vein is placed. This needle may have to be further secured to stay in place by a "clamp" to prevent draining of the blood distally from the inserted needle.

b. When sterile discs are used, the umbilical cord is lead through the central disc opening for it. After that, the sterile plastic cover for placenta is placed on the maternal surface of the placenta to secure the position of the placenta in the round box while the lower plate discs are rotating.

4. When this is completed, the transparent firm plastic box is firmly closed.
5. Mechanism for shaking of the COB is tested.
6. Computer is put on the "ON" position at that time of the device is started after all displays are checked to be properly presented.

At that point (or even before that time) the following information may be entered into the computer or may have been already entered:
    a. Internal identification of the procedure for appropriate Blood Bank is placed into the computer.
    b. Name of the mother delivering the baby and the placenta is entered.
    c. Name of the baby whose placenta is processed is entered. If the name is not known at that time name like "Baby Boy Smith" is entered.
    d. Time of delivery of the baby is entered.
    e. Time of delivery of placenta is entered.
    f. Weight of the placenta is recorded. The placenta is to be measured and this as well as the weight of the placenta is recorded.
    g. If the option of a sterile plate (Fig. A.3.f.) is used, the placenta is covered with the sterile plastic sheet described under A.7. to protect it from contamination by the compression chambers and then the equipment is closed.
    h. If the pressures in the compression chambers are not predetermined, the operator enters the initial pressure of the most peripheral bag; differentiation of the pressures in the consecutive bags is also entered as well as the time for each pressurization.
    i. Time is automatically entered by the computer at the actual start of the operation and the operator does not do this. However, the time of the start of the operation is entered by the computer when the operator starts the operation of collection of the blood.

The operator has also a choice to start the operation of PBE as is suggested by the manufacturer (default procedure).
7. After that PBE is closed firmly.
8. After the final inspection that all this is properly done, the operator starts with the operation of PBE. This will simultaneously start pressurizing the inflation bags, develop negative pressure in COB, started rotation of the lower plate and the gentle shaking of COB will commence. The operator will be able to see the blood flowing into the commercially supplied sterile bag for the collection of the blood.

9. When the extraction of the blood from the placenta and the umbilical cord is finished, PBE compression bags are deflated. Operator may manually "milk" the remaining blood from the umbilical cord into the collection bag. However, if the operator selects to extend the extraction of blood for another short period of time, the operator has to give such order before PBE automatically terminates the operations. This choice of the operator is limited and it can't be done longer than the design of the software allows it. The computer gives a warning about that prior to termination of operations.

10. The operator opens COB and seals the tubes delivering the blood. The placenta is placed for disposal. The needles are removed from the umbilical cord are placed into disposal area. The sterile bag with the collected blood is appropriately handled for shipping and further processing as per standard procedures. PBE and COB are cleaned for the next collection and stored after that.

11. The operator gives the order that weighing of the blood is done and this information is delivered to the computer. After that the complete report is compiled.

Suggested pressures for operation as well as the timing are as follows:

A. Positive pressure sequence in the bags for pressurization of placenta is to be in the levels of the physiologic pressure for human conditions. Thus, it is recommended that the positive pressure as a general rule is between 20 mm Hg to no more than 200 mm Hg. However, recommended usual maximal pressure should be between 120 to 150 mm Hg which is sufficient to extract most of the blood from placenta into the umbilical cord vein and then to collect it into the commercial collection blood bags. Also, it is important to accept that the pressure in multiple compression chambers are always higher at the periphery of the placentas and lower toward the center of it. Gradations of these pressures may be determined empirically when the extractions are done. Thus, each operator will have to select the lowest as well as the highest pressures the equipment will be operated at.

B. Negative pressure in COB is from −5 mm Hg to no more than −50 mmHg.

There will be several sequences of pressurization of the compression chambers. There will be two choices of these pressurizations:

1. One choice is that compression chambers are pressurized sequentially in the order from the periphery toward the center of the placental container. Peripheral chambers may be pressurized first and the remaining central compression chambers are not pressurized at all. When the last central compression chamber is pressurized for the time programmed for this, all compression chambers are depressurized. In the next cycle of pressurization, the first, the most peripheral chamber is again pressurized or stays pressurized all the time and the rest are not. Then the second one is pressurized along with the first one. However, the pressure in the second chamber is to be lower that in the first one and so on. This way the blood in the collection vein are able to be "pushed" from the area of the first chamber into the second one, then from the first and second area to the third one centrally, etc. The same is to be done until the full cycle of pressurization is done with all chambers.

2. The other choice is that all compression chambers are gradually pressurized (again with lower pressures centrally) and they stay pressurized but in the next cycle the pressure is increased in the most peripheral chamber and gradually raised in the subsequent chamber toward the center of the equipment.

The selection of these two ways to pressurize the equipment will be the choice of the operators and their supervisors.

Figure 1:
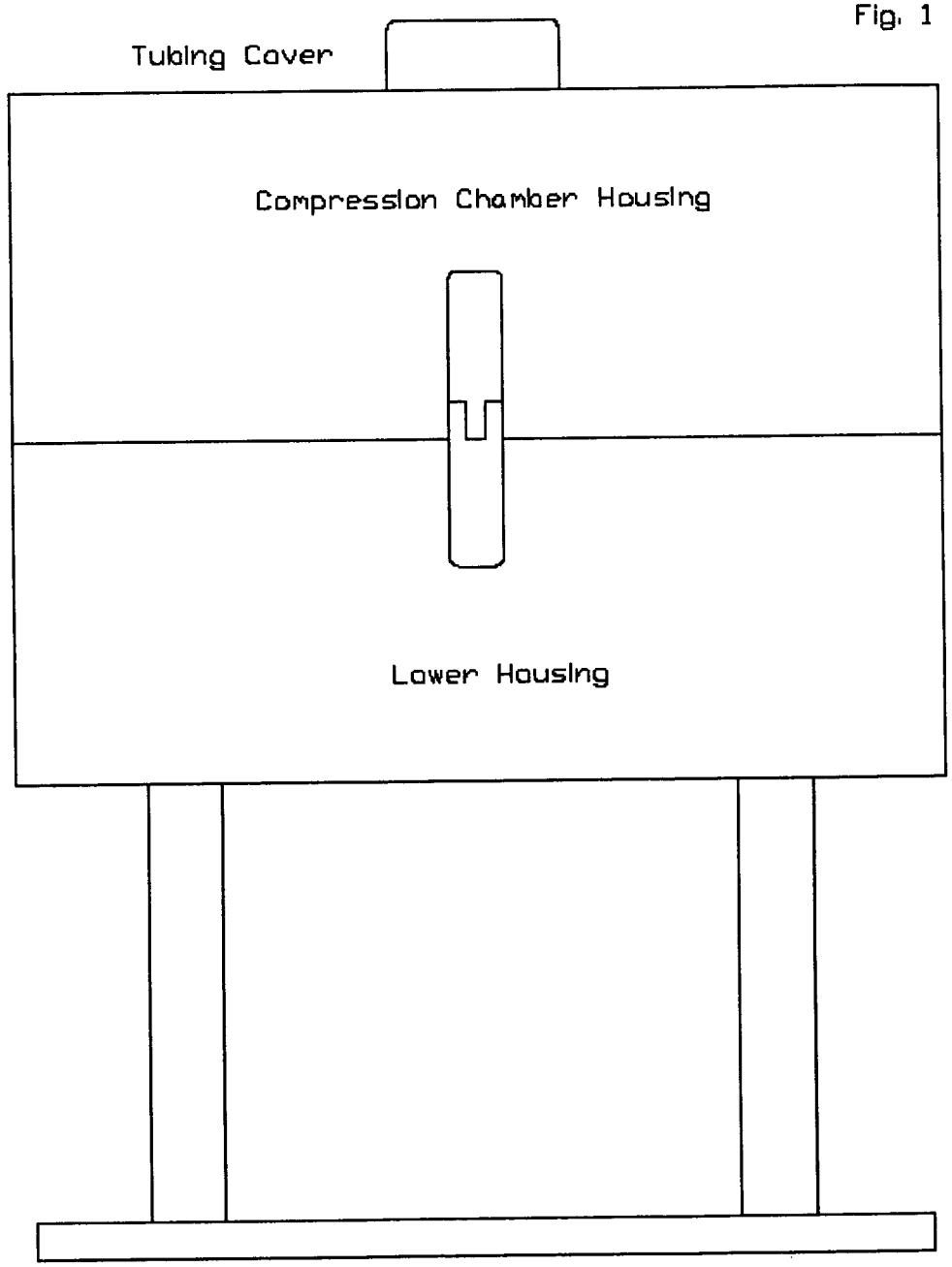
FIG. 1. The picture represents the front view of the round firm box for placement of the placenta.
Figure 2:
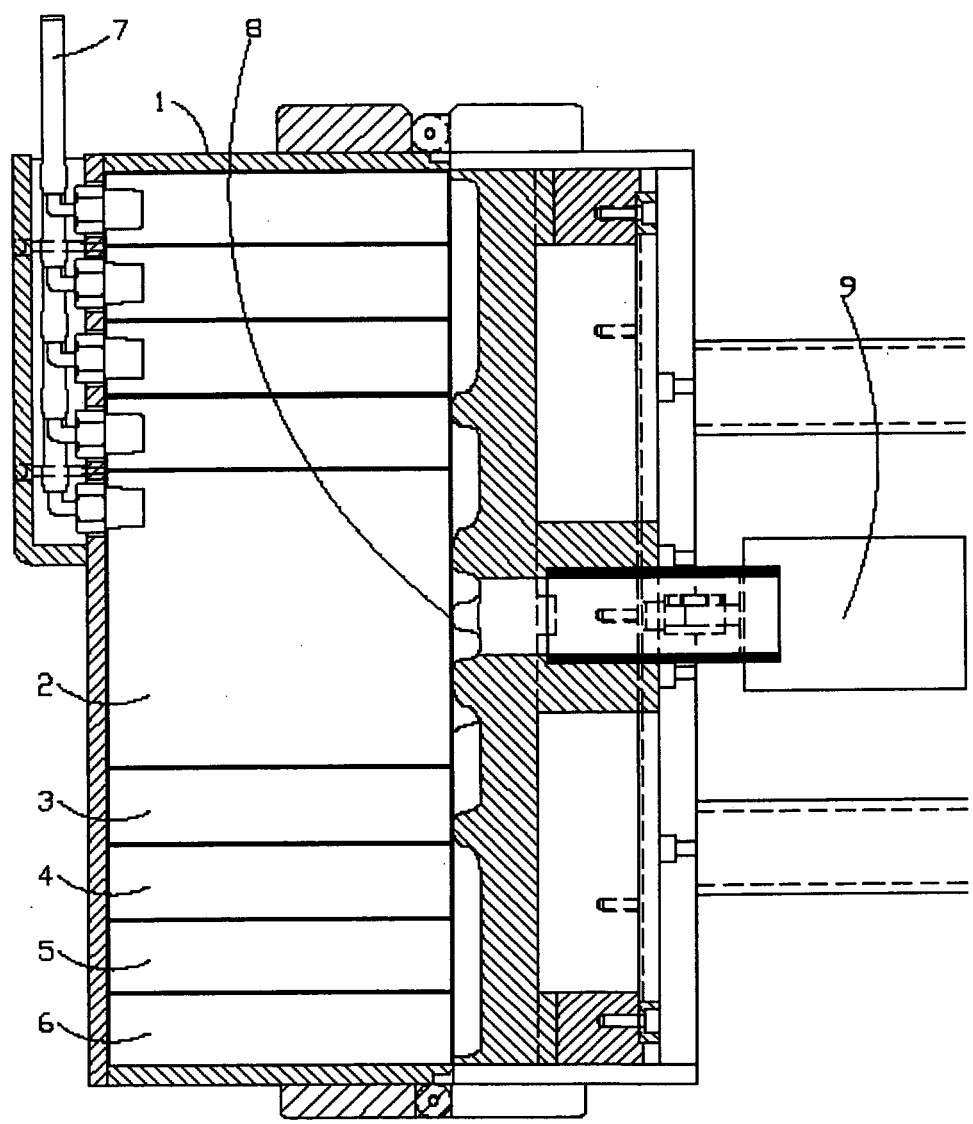
FIG. 2. This picture represents the side view of the round firm box (#1) for placement of the placenta between the compression chambers and the upper surface of the lower disc (#8).
Figure 3:
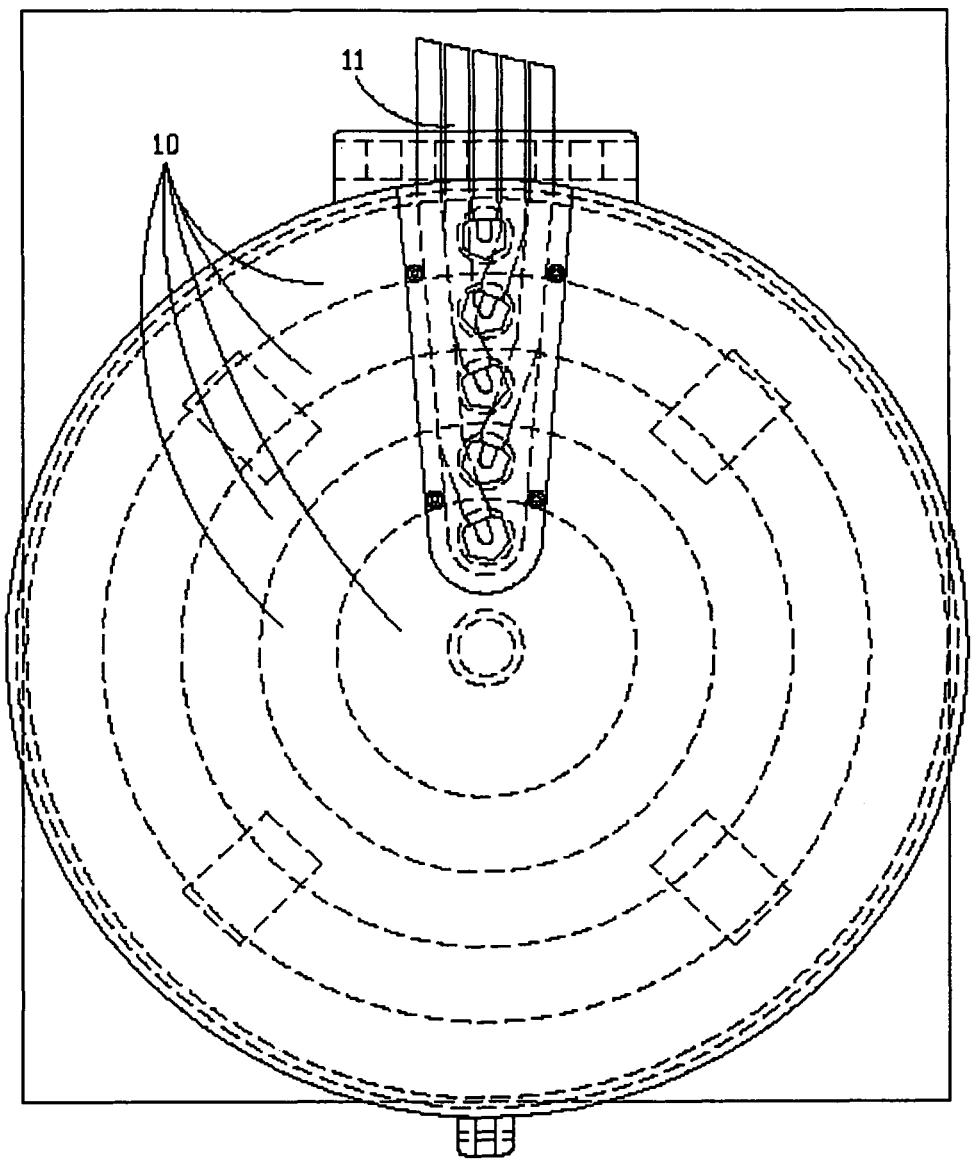
FIG. 3. This is the view from above of the firm plastic box for placement of placenta showing five concentric chambers (#10) and the area where tubing for pressurization of compression chambers are placed (#11).
Figure 4:
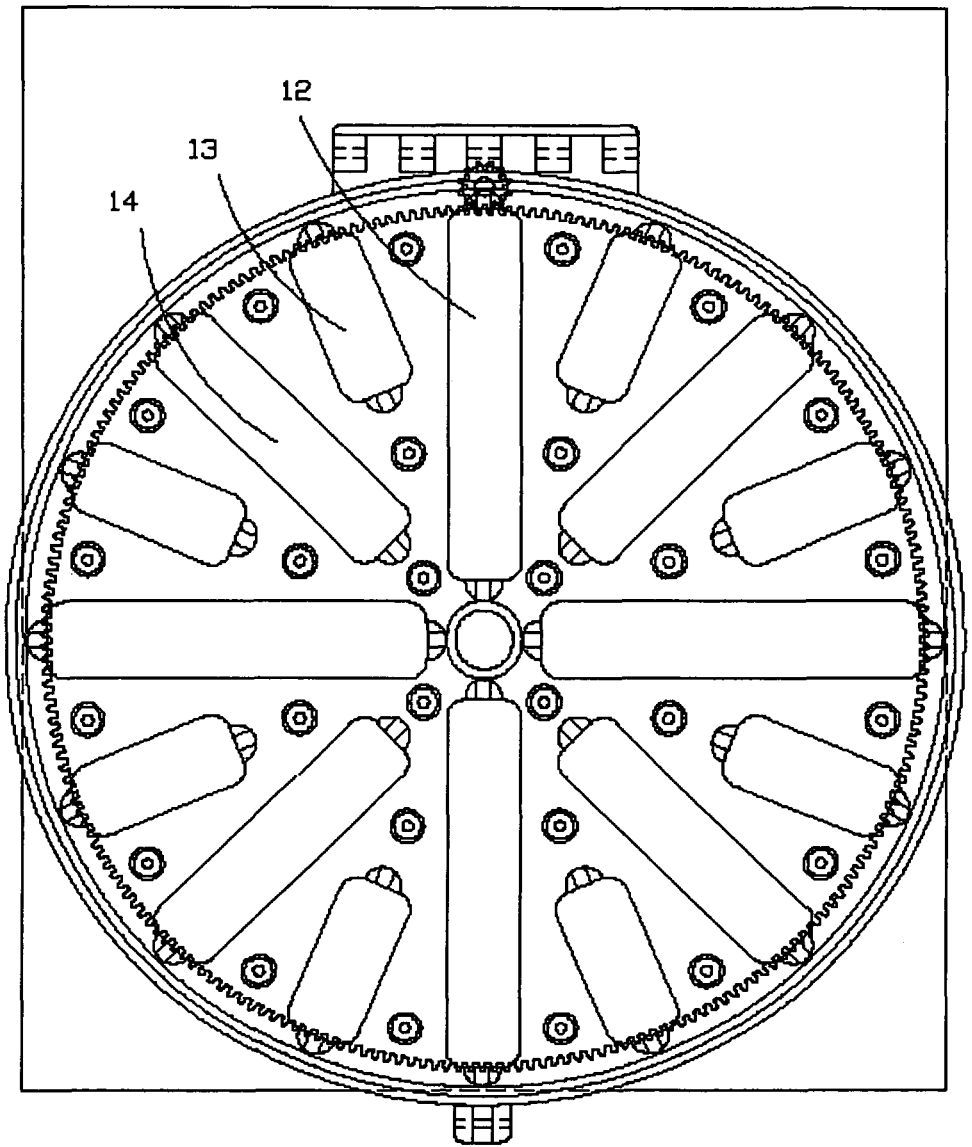
FIG. 4. This picture represents one choice for lower plate of PBE.
Figure 5:
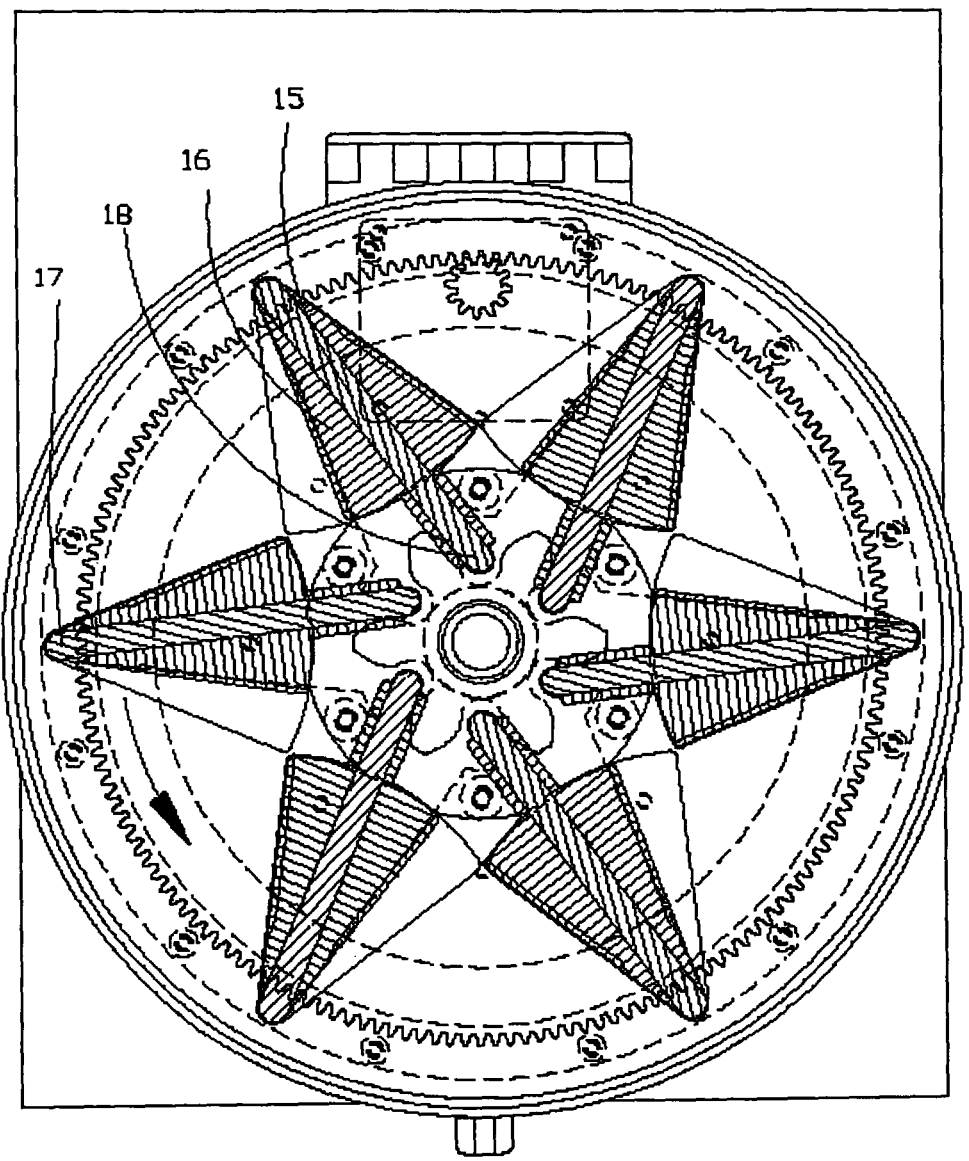
FIG. 5. This picture shows the option of the lower plate having three sections.
Figure 6:
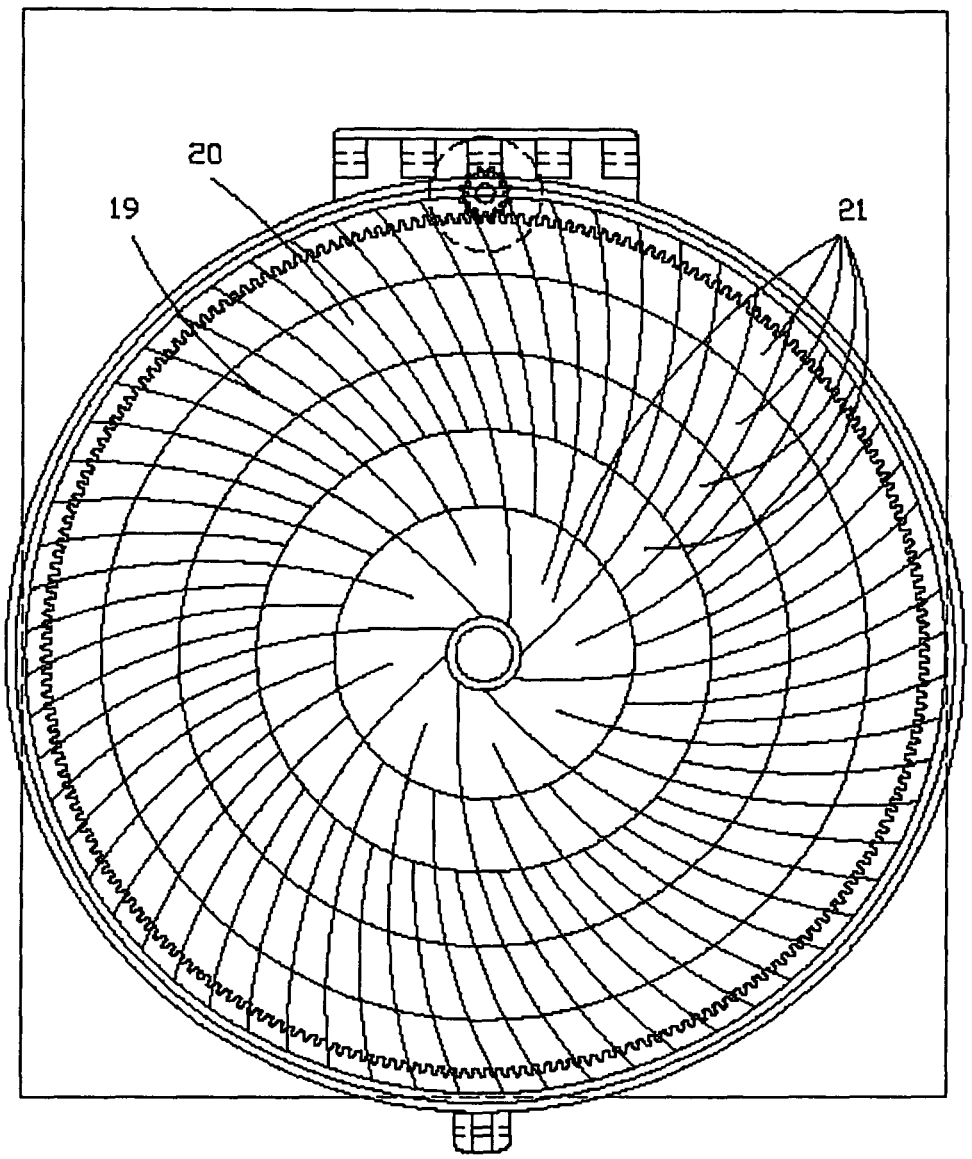
FIG. 6. This picture shows the third choice of the possible lower discs to be constructed as a single disc.
Figure 7:
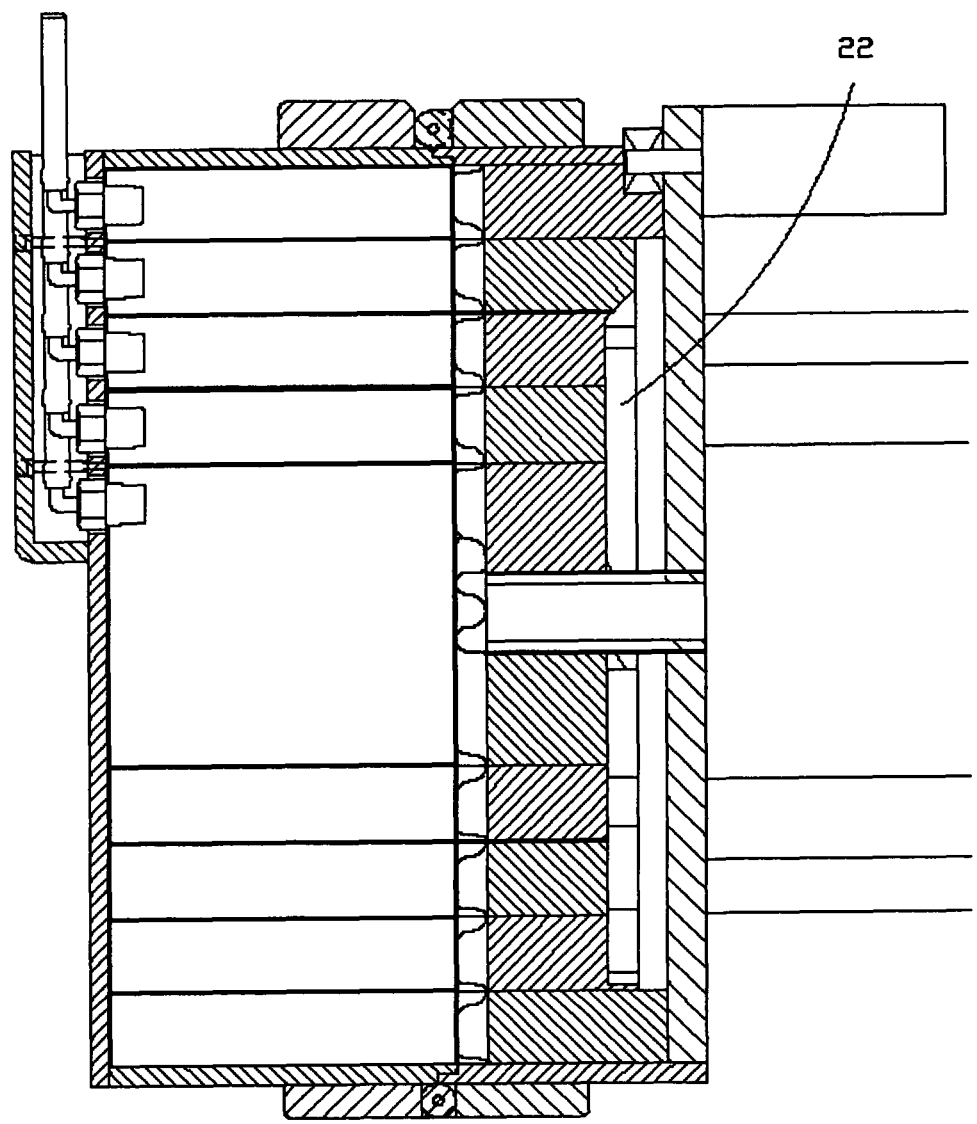
FIG. 7. This picture shows the cross section of the firm plastic box for placement of placentas when fourth modification of the lower plate is used.
Figure 8:
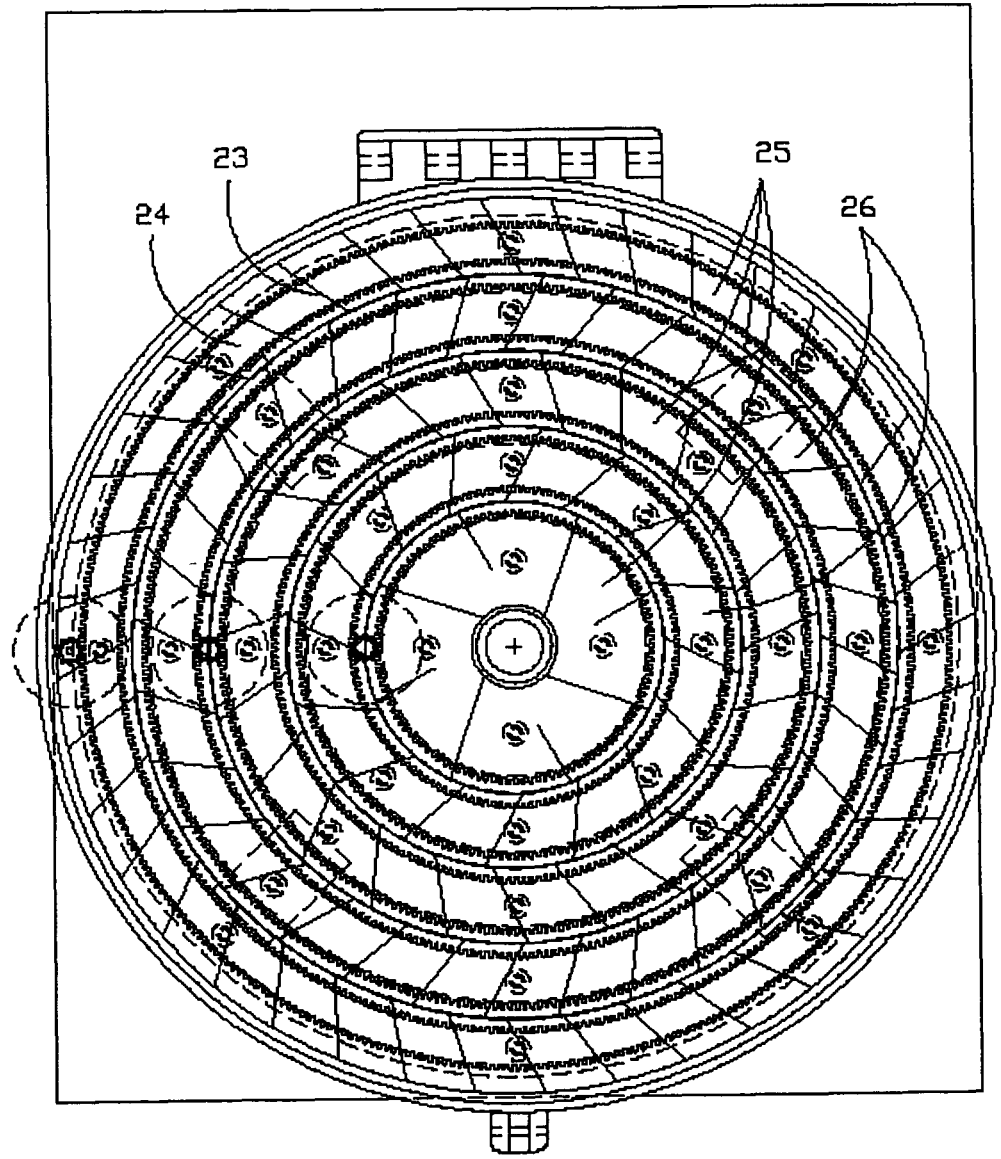
FIG. 8. The fifth choice of the lower plate is composed of several concentric rings, each to be moved in the opposite direction from the previous and the next concentric ring.
Figure 9:
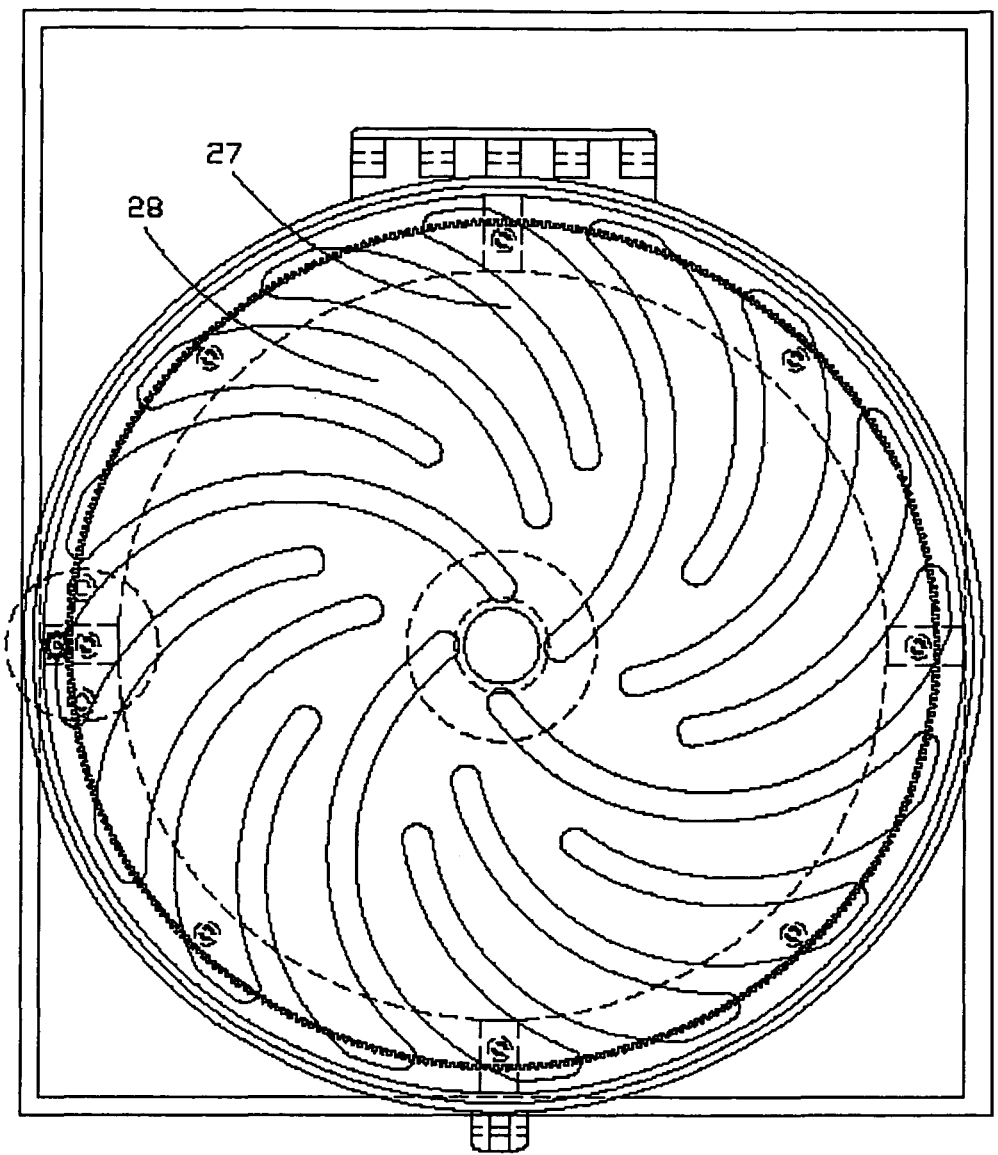
FIG. 9. This picture shows another choice of the lower plate constructed of two plates.
Figure 10:
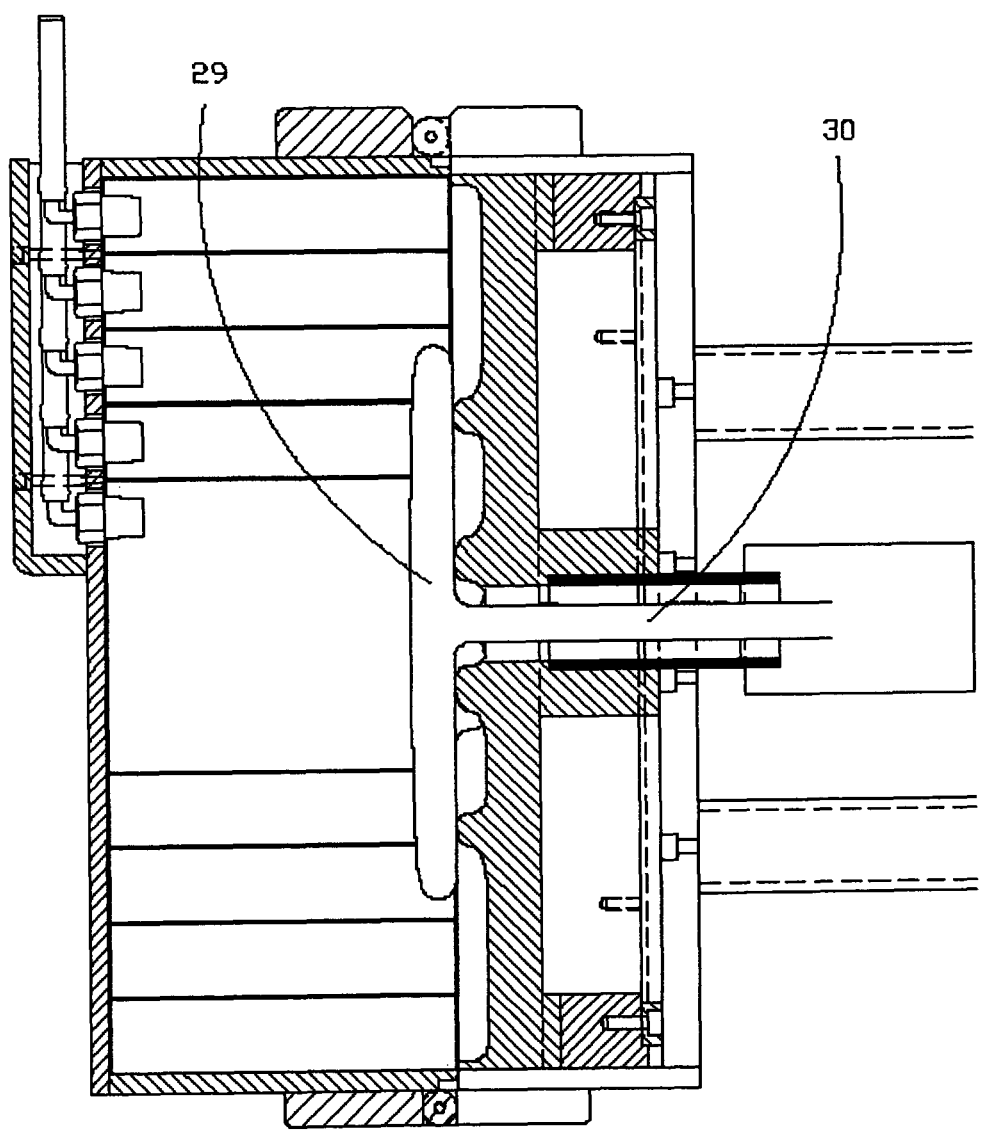
FIG. 10. This picture shows the positioning of the placenta (29) and umbilical cord (30) in the plastic box with five compression bags above it.
Figure 11:
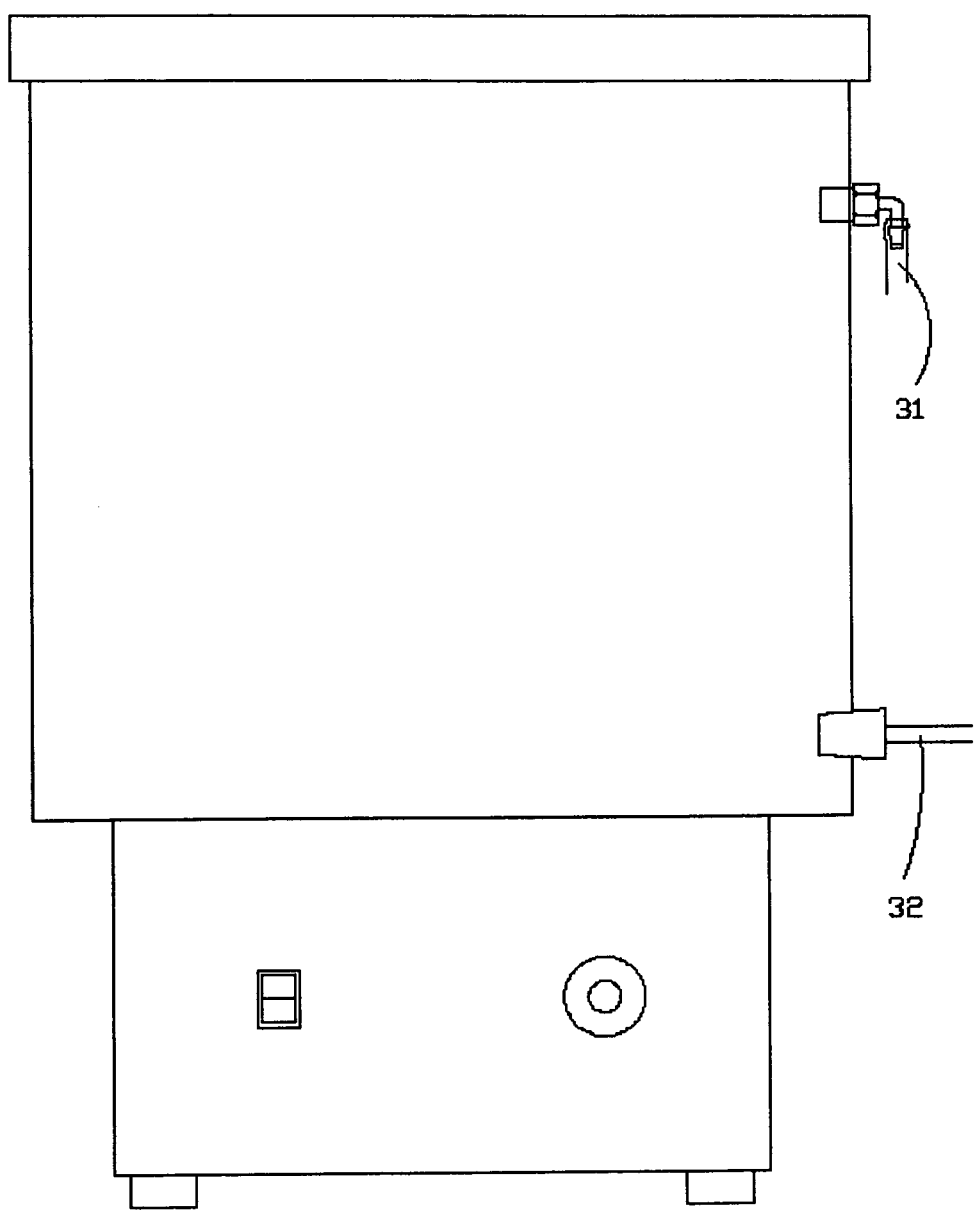
FIG. 11. This is the picture of the Collection of Blood Box, in the text referred to as COB.
Figure 12:
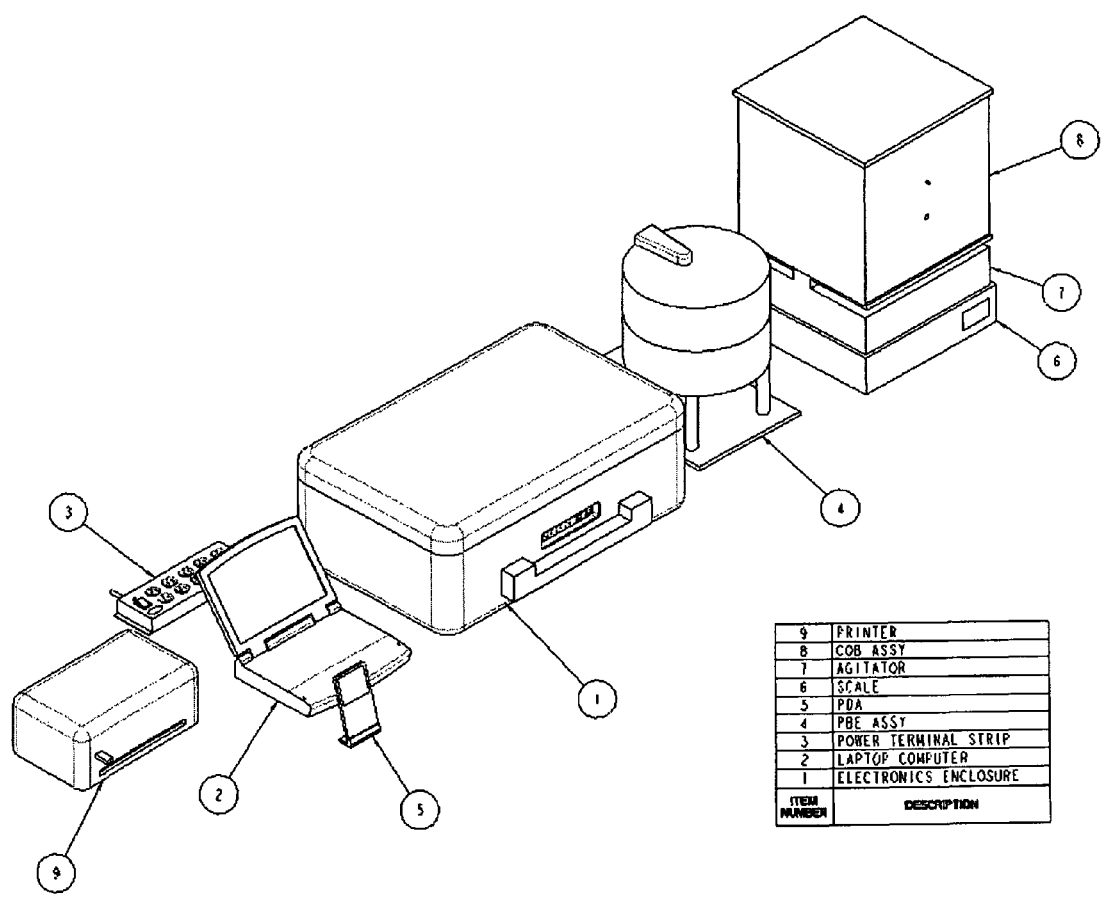
FIG. 12. This picture represent the entire set of different parts of PBE and COB. These parts may be integrated but here are presented separately to illustrate their different functions.

What is claimed is:

1. A placental blood extractor for collection of placental and umbilical cord blood, said blood
    extractor comprising of:
    a. a round plastic firm outside box for placing placentas composed of an upper part and a lower part designed to be closed when the placenta is placed in it,
    b. a plurality of soft plastic compression chambers attached at the upper part of the box and concentrically lining said box,
    c. pumps attached to each plurality of compression chambers,
    d. monometers for determining the pressure to be applied through soft plastic compression chambers connected to the pumps and compression chambers through plastic tubing,
    d. several different type of rotating plates for mechanically facilitating the flow of blood from periphery of placentas extracting the blood from the collecting veins on the fetal side of the placenta and "pushing" it toward the centrally positioned umbilical cord veins,
    e. sterile bag for holding a placenta, said bag having an upper part for placing the placenta in the bag to be closed before extraction of the blood begins and said bag for the placenta being mounted within said firm plastic box which has a central hole on its lower side on the center of the disc for mechanically removing the blood and directing the blood from the collecting veins on the fetal side of the placenta to the umbilical cord vein and the bag having a central leader for umbilical cord on its lower side; the firm plastic outside box for placing placentas is then closed after the leader containing the umbilical cord is lead through the hole in the box containing the plates under "d", and then said bag with placenta placed between the compression chambers above and one of the selected discs which will mechanically move the blood from the collecting veins toward the central umbilical cord vein.

f. When a single rotating disc is used, instead of sterile bags for placement of the placentas, the placentas will be covered with sterile plastic sheets with protrusions to hold the placenta in place while the plate is rotating and another sterile plastic sheet between the placenta and such lower disc or rings is being used.

\* \* \* \* \*